United States Patent
Fiz

[19]

[11] Patent Number: 6,083,226
[45] Date of Patent: Jul. 4, 2000

[54] BONE FIXATION DEVICE AND TRANSVERSE LINKING BRIDGE

[76] Inventor: Daniel Fiz, Parana 754, 9th Floor "B", Buenos Aires, Argentina

[21] Appl. No.: 09/154,998

[22] Filed: Sep. 17, 1998

[30] Foreign Application Priority Data

Apr. 22, 1998 [AR] Argentina ............... P 98 01 01861

[51] Int. Cl.⁷ ................................... A61B 17/70
[52] U.S. Cl. ............................................. 606/61
[58] Field of Search ............... 606/61, 60, 72, 606/73; 623/17

[56] References Cited

U.S. PATENT DOCUMENTS

| | | | |
|---|---|---|---|
| 5,275,600 | 1/1994 | Allard et al. | 606/61 |
| 5,312,405 | 5/1994 | Korotko et al. | 606/61 |
| 5,344,422 | 9/1994 | Frigg | 606/61 |
| 5,474,551 | 12/1995 | Finn et al. | 606/61 |
| 5,522,816 | 6/1996 | Dinello et al. | 606/61 |
| 5,569,247 | 10/1996 | Morrison | 606/61 |
| 5,609,592 | 3/1997 | Brumfield et al. | 606/61 |

*Primary Examiner*—Michael Buiz
*Assistant Examiner*—Vy Quang Bui
*Attorney, Agent, or Firm*—Darby & Darby

[57] ABSTRACT

Bone fixation element and transverse linking bridge for a spinal column fixation assembly, in which the fixation element and the bridge allow to accommodate more easily the connections between the parts forming the bone fixation assembly, which would make difficult the alignment and interconnection of each of the assembly connecting parts, the fixation element comprising a hook or screw presenting an intermediate portion of spherical form that may be coupled to a seat portion of a coupling piece between the fixation element and the bar of the fixation assembly. The transverse linking bridge comprising one or two bridge parts which have at their ends a coupling hook in which a pivoting spherical insert is placed, which adjusts the deviations of the respective bar during fastening.

20 Claims, 3 Drawing Sheets

BONE FIXATION DEVICE AND TRANSVERSE LINKING BRIDGE

BACKGROUND OF THE INVENTION

1. Field of the Invention

The present invention relates to a bone fixation assembly and to a transverse linking bridge for spinal fixation assemblies, the invention being related in particular to the field of the devices widely used for correcting the position of the spine or spinal column.

2. Description of the Prior Art

It is well known, under some circumstances—due to natural malformations or surgery—that it is necessary to correct the deformation or incorrect position of the spine to bring the spine back to its natural and correct position. The spinal column preferably has an extension along a vertical line as seen from the front of a human being and a "S" shape as seen from the side. Due to different circumstances the mentioned "S"-form as well as the vertical line are deformed because of a displacement of the vertebrae one with respect to the other. This deformations may produce displacements, fractures, tumors and infections which could be prevented correcting the alignment of the vertebrae through the use of devices that compress, distend or rotate all or parts of the vertebrae that form the spinal column in relation to one or all spatial reference axes X, Y and X.

Several mechanical devices or arrangements or assemblies have been developed to this end. Generally, all of these consist of sets of screws and rods, as well as fixation plates that form very complex mechanical systems. The older ones typically used a rod or rigid bar that fixed the spine by means of screws inserted in the pedicles to fasten the bar. Then the rod is bent to the desired arrangement according to the corresponding axis to bring the column into its normal position. In all cases, the screws fixed to the vertebrae must allow the fixation of one or more rods that have to pass through and be threaded in some type of connector to each one of the screws. It is easy to see that it is very difficult to make a rigid bar pass through a plurality of screws that probably will not be aligned in the desired position and that will also not show its connector receptors oriented in alignment to allow the passing through of a bar or rod. This is very difficult when the corrections at the spinal column must be made in the three dimensions of space, i.e. with respect to the three axes X, Y and Z. Thus, the screws that are fixed over the vertebrae usually have to be removed and placed again to find a new orientation, and this may cause a considerable damage to the bone tissue of the vertebrae in which the screw is being threaded. Sometimes there is not enough space to make this reorientation and this means a risk for the patients health because there exists the possibility of fracturing the most fragile parts of the vertebrae with the resulting consequences.

Among the several fixation arrangements and assemblies for the spinal column it can be mentioned the one disclosed in U.S. Pat. No. 5,498,262 which defines an assembly consisting of a pair of bars that pass through coupling devices rigidly fixed by means of a screw to the bar while at the other end they are fixed to a clamp through which rigidly passes a screw threadably inserted into the corresponding vertebra. In the case of the fixation between the connector and the rod as well as in the case of the fixation between the connector and the bone fixation screw, i.e. the one that is inserted in the vertebra, the threaded holes allow the insertion of the screw only in one position, which makes the assembly of the arrangement in the spinal column too rigid with a reduced margin of movement, and accordingly, with a reduced margin of error for the surgeon while positioning the screws.

Other devices with some improvements relating to the assembly of the fixing screw, e.g. in inclined form, are provided, like the one disclosed in U.S. Pat. No. 5,306,275, in which the fixation of the screw in relation to the extended bar between screws is rigidly obtained by means of a perforated stem which receives the bar and which fixes the same against the screw by means of a nut. However, as already mentioned, the connection is rigid not allowing an omni-directional movement.

U.S. Pat. No. 5,129,900 provides an vertebrae fixation arrangement for the spine that includes a coupling part presenting at one end a receptor bore of one of the spine correcting bars, which is secured inside the connector part by means of a fastener or screw while at the other end it presents a substantially elongated opening for passing through a bone fixation screw. This elongated opening allows the bone fixation screw to accommodate along the axis of this opening, whereby the distance between the fixation screw and the rod may be variable according to the length of this opening. However, this elongated opening does not allow the accommodation of a screw that has been positioned in angular o deviated form with respect to the straight line passing through any longitudinal point of said opening. That means, that if a bone fixation screw would have been situated in deviated form with respect to its pre-established path, the longitudinal geometrical axis of the screw would not pass through the opening foreseen in the connection part due to an angular difference.

To accommodate angular positions of the bone fixation screws, some connecting assemblies provide beveled washers in different angles so that the inclination of the screw does not hinder the tight fastening of the coupling member, allowing the nut in the screw to integrally rest on and secure the fastening screw and the coupling member to the rod of de spinal fixation. Again, this is a device that allows only a good seat between the nut of the screw and the fastening element provided that the screw may accommodate its inclination inside the opening of the fastening element. Even so, the provision of nuts and washers with inclined surfaces only makes more complicated the assembly of the arrangement and provides too many parts that are not very desirable for the safety of the patient.

In the fixation assemblies in which two paralell bars fixed to both sides of the spinal column vertebrae are used, the bars are connected one with respect to the other by means of interconnecting transverse bridges. This interconnecting bridges present different arrangements which allow them to vary their length in order to accommodate to the spacing of the longitudinal bars of the assembly, as well as to any angular difference or pivot movement of the bars with respect to a transverse axis of the same. That means, there are bridges consisting of two telescopic parts that may pivotally move one relative to the other. The bridges may be elongated by means of these telescopic parts that are adjustable one with respect to the other or by means of extensible parts with threaded rods of nut and counternut with a central hub for the contraction and expansion of the bridge parts. These type of bridges are disclosed, inter alia, in the U.S. Pat. Nos. 5,522,816, 5,084,049 and 5,498,262. However, neither of these interconnecting transverse bridges between corrective bars of the spinal column allow to adjust the bars one with respect to the other modifying not only its spacing, but also its rotation with respect to a transverse axis to the same and its angle of difference of parallelism, i.e., the variation of the angle in the plane that contains the same.

In view of the above mentioned, it would be desirable to have a bone fixation element for spinal column fixation arrangements that would offer more possibilities of assembling the arrangement by means of an multi-directional adjustment in its connection with the arrangement, as well as to have a transverse interconnecting bridge for the bars of the spine fixation arrangements that would allow also a not so rigid assembly with respect to the interconnection of the different parts of the fixation arrangement.

3. Summary of the Invention

It is therefore one object of the present invention to provide a bone fixation device for spine fixation assemblies that allows to connect more freely the bone fixation element to the bars of the fixation assembly, even in spite of the position deviations between the same, deviations that would difficult the alignment and interconnection of each connecting part of the arrangement, as is the case in the previous art.

According to an aspect of the invention, a bone fixation element is provided that allows to accommodate more easily each of the parts forming the bone fixation assembly at the moment of the interconnection of the same, whereby the fixation element comprises a hook or screw that presents an intermediate portion of spherical form that may be coupled with a seat portion of a coupling piece between the fixation element and a bar of the fixation assembly.

More precisely, it is an object of the invention to provide a bone fixation element for a spine fixation assembly of the type which comprises a screw or hook with a threaded portion of fixation to the bone, vertebrae or the like, whereby the element may be connected to a coupling piece by means of a fastening nut, while the coupling is fixed to a bar of a pair of bars of the spine fixation arrangement, said fixation element presenting an intermediate portion at least partially spherical and a top portion for the threading of said nut, and said coupling piece presents a portion of receptor seat at least partially spherical, which receives said at least partially spherical portion of screw, said seat portion presenting a passing through bore for said upper portion of the fixation element.

Another object of the present invention is to provide a transverse interconnecting bridge for bars of spine fixation assemblies that allows to connect the bars transversally one with respect to the other, even in spite of the position deviations in each plane or angle between the same, deviations that would make difficult the alignment and interconnection of each of the bars and the other connecting parts of the arrangement.

According to one aspect of the invention a transverse interconnecting bridge is provided between the bars of the spine fixation assembly, the bridge including one or more parts that have at its ends a coupling hook in which a pivoting spherical insert is located which insert accommodates the deviations of the respective bar at the time the fixation is carried out.

More specifically, the invention provides a transverse interconnecting bridge for bars of a spine fixation assembly, of the type that includes only one part or at least two parts that may be coupled to form a bridge of adjustable length, the bridge presenting ends in form of hooks to allow the coupling to respective bars of the fixation assembly, one of said ends in form of hooks presenting at least an insert of outer surface at least partially spherical pivotally mounted inside of said hook, said insert presenting a fitting inner surface for each of said bars.

The above and other objects, features and advantages of this invention will be better understood when taken in connection with the accompanying drawings and description.

BRIEF DESCRIPTION OF THE DRAWINGS

The present invention is illustrated by way of example in the following drawings wherein.

DESCRIPTION OF THE PREFERRED EMBODIMENTS

Figure 1:
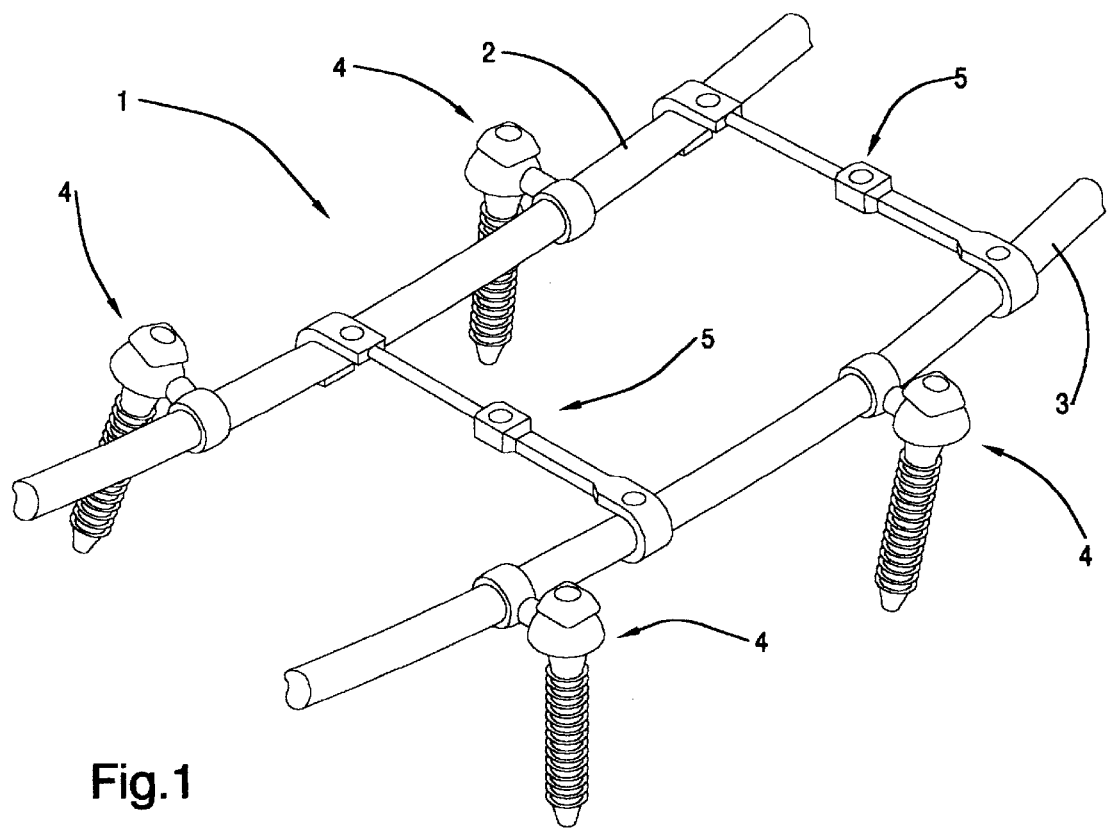
FIG. 1 shows a general perspective view of a spine fixation assembly that includes the fixation elements and the linking bridges according to the invention.

Now referring in detail to the drawings, FIG. 1 illustrates a general view of the bone fixation assembly for the spinal column, which assembly is provided with the advantages of the present invention, said assembly being shown in perspective and is indicated with the general reference number 1. The bone fixation assembly consists of two bars which run preferably parallel to each other but that will accommodate to the corrections that will be made to the vertebrae. On each bar 2, 3, bone fixation elements 4 are located with the aim of fixing to the bone or vertebrae and fasten to the bars 2 and 3 to maintain an alignment and a stable fastening between the vertebrae of the spinal column that have to be corrected in their position. To cooperate with the retention of the bars 2 and 3 and hence to maintain the desired vertebral alignment, the bars 2, 3, are connected to each other by means of linking transverse bridges 5, of fixed length or preferably of variable length, which also incorporate the advantages of the present invention.

Figure 2:
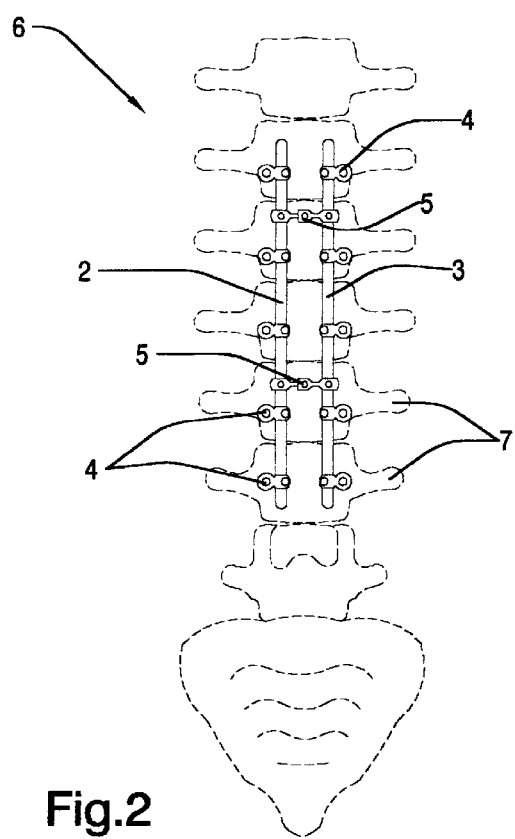
FIG. 2 shows an elevation view of part of the spinal column with the fixation assembly located at the same.
Figure 3:
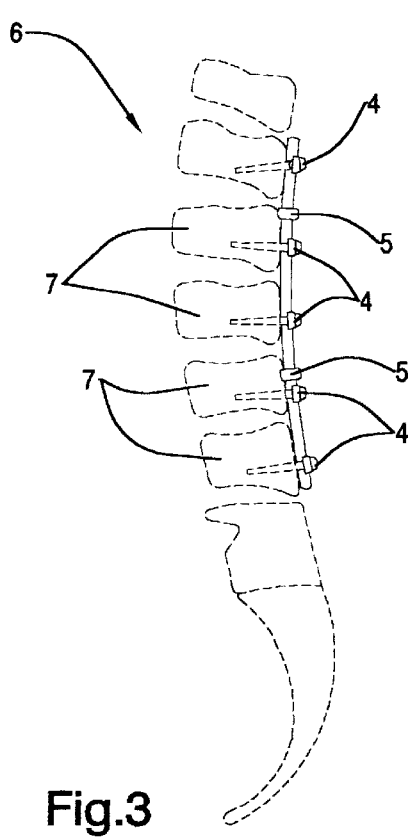
FIG. 3 shows a side view of the spinal column of FIG. 2.

As can be seen in FIGS. 2 and 3, the spinal column 6 is illustrated from the front and the side in each of the Figures respectively and shows the fixation assembly of FIG. 1 placed with therapeutic aims on the column 6. To this end, the fixation elements 4 are threaded over each of the vertebrae 7, and for this, as will be described in the following in detail, and in particular with reference to the FIGS. 4 and 5, the fixation element has a threaded elongated body which is inserted in the bone mass of the vertebrae 7 to get attached to the same. Although two fixation elements 4 for each vertebrae are illustrated, the quantity will depend on the problem to solve in the spinal column, on the size of the vertebrae, etc. Each of the rods 2–3 will have the necessary length, which will depend on the section of the spinal column that has to be treated or corrected. The linking bridges 5 will be placed on suitable distances to arrange the stiffened assembly in the desired manner. The materials used for the bars or rods, the fixation elements and the linking bridges are biocompatible materials, e.g., stainless steel. The material used for the bars will also enable the same to be handled in such form that they may be bent to maintain the vertebrae 7 aligned according to the desired spatial relationship to give the spinal column the desired curve, in all or in any of the three possible anatomical planes. As can be seen in the following in detail, when the bone fixation elements and the transverse linking bridges according to the invention are described, the installation of the assembly illustrated in FIGS. 1 a 3 will be much easier due to the multi-directional adjustment that allow the particular structural and functional characteristics of the bone fixation element 4 and of the transverse linking bridge 5.

Figures 4, 5, 6:
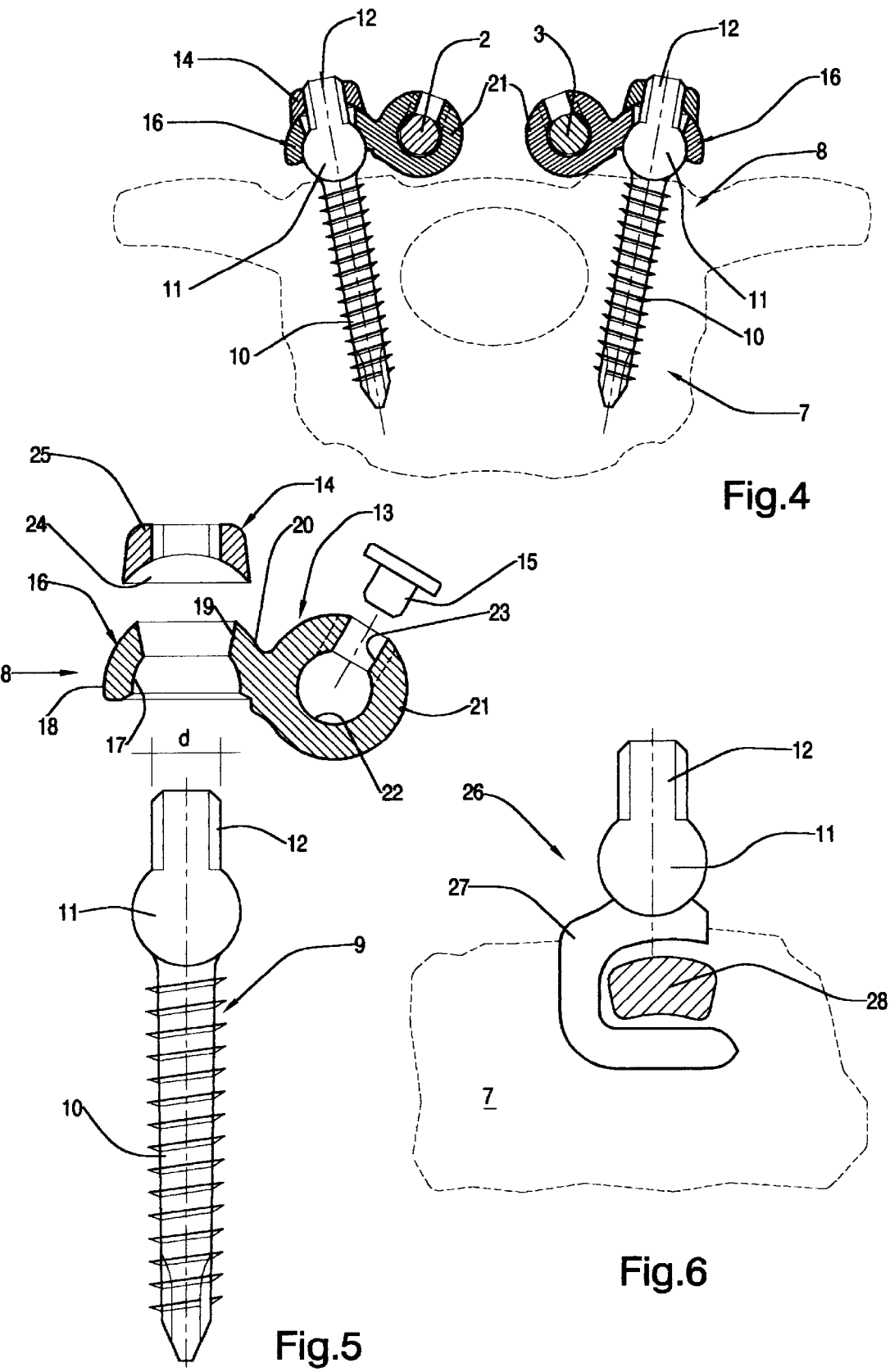
FIG. 4 shows a cross-sectional view of a vertebra in which two fixation elements and the respective bars of the fixation assembly are fixed according to the invention.
FIG. 5 shows an elevation and exploded view of a fixation element, in particular a screw, according to the invention.
FIG. 6 shows an elevation view of a fixation element according to the invention, particularly having another configuration, forming a hook and located in a vertebra.

With reference to the bone fixation element 4 provided by the invention, the same is clearly illustrated in FIGS. 4, 5 and 6; FIG. 5 illustrates an embodiment in which the bone fixation element adopts the configuration of a screw while in the embodiment of FIG. 6 the bone fixation element adopts the form of a hook to achieve the attachment to a laminar part of a vertebra. The bone fixation element with screw form indicated with reference number 8 comprises a screw body 9 consisting of a lower threaded portion 10 that will vary in form and size according to the application of the screw as well as its screw thread. Immediately above the threaded fastening portion 10 an intermediate portion at least partially spherical, but preferably completely spherical 11, is placed, over which, following a longitudinal geometrical axis of the screw 9, a threaded upper portion 12 is placed. The screw 9 may be inserted in the body of the vertebra 4 by means of any suitable tool, either a special tool or a key capable of being inserted into a faceted cavity which may be provided in the portion 12 to remain embedded inside the vertebra 4 in the form illustrated in FIG. 4. A coupling piece substantially consisting of two parts will be connected to the screw 9 and will be mounted particularly through the threaded portion 12 to rest over the spherical intermediate portion 11. The coupling piece 13 comprises a seat portion 16 in usually spherical form or a spherical cap which has a concave inner surface 17 and a convex outer surface 18 disposed on the upper part or polar zone of the cap a bore 19 that has a diameter greater in excess than the diameter d of the threaded portion 12 of the screw 9.

The seat portion 16 of the coupling piece 13 is linked through a bridge section 20 to the fixation and fastening portion 21 intended to get fixed to each of the bars 2 an 3. To this end the fixation and fastening portion includes a bore 22 intended to receive the bar as illustrated in FIGS. 1 and 4. More precisely the bar 2 or 3 is retained inside the bore 22 due to the provision of a screw 15 that is threaded in a bore 23 provided in the fastening portion 21. Although the coupling piece 13 has been defined as consisting of a fastening portion 21 of spherical form and closed as a loop, linked almost directly to the seat portion 16 with an interconnecting bridge section 20, depending on the desired configuration for the fixation arrangement 1, the bridge section 20 may adopt the form of a bridge of greater length while the bar fixation portion 21 may be shaped in open form, i.e. the transversal section of the portion 21 may have the general form of a "C".

Once the threaded portion 12 passes through the bore 19 of the seat portion 16, i.e. when the concave surface 17 rests completely on the spherical intermediate portion 11, the fastening screw 14 is placed, presenting a coupling concave inner surface 24 intended to rest on and be coupled with the convex outer surface 18 of the seat portion 16 as is clearly illustrated in the FIG. 4. The fastening nut 14 may have a faceted outer surface 25 that makes easier the operation due to a fitting wrench of the type known as socket wrench. Otherwise, any other wrench already known in this matter may be used.

According to a second alternative illustrated in FIG. 6, the fixation element 8 may adopt the form of a hook indicated with the general reference number 26 and in which the same reference numbers have been used for the threaded top portion 12 and the spherical intermediate portion 11, as they remain the same for the embodiment in form of a screw illustrated in FIG. 5. The difference of the embodiment of the screw is that instead of providing a threaded portion 10 (FIG. 5) a hook portion 27 is provided, the function of which is to remain attached over the laminar part 28 of the vertebra 4. This applies when, under particular circumstances, a screw cannot be inserted in the desired zone of the vertebra in which case the fixation element 8 is attached to the laminar parts 28 of the vertebra by means of the hook 27. Furthermore, the assembly between the fixation element 8, in a screw or hook form, and the coupling piece 13 and the nut 14 are the same in both cases.

Unlike the fixation elements known, the spherical intermediate portion 11 and the seat portion 16 allow a spherical assembly of the arrangement which provides an omnidirectional connection making it easier for the surgeon to accommodate the pieces once the screws or hooks have been placed over the vertebrae. The bore diameter 19, which, as above mentioned, is greater in excess of the diameter d of the upper threaded portion 12, allows the spherical portion 11 to rotate omnidirectionally inside the seat portion 16 against the concave inner surface 17 according to a conical angle of at least 24°, i.e., of at least 12° at each side of a longitudinal geometrical axis of the screw that passes through the center of the bore 19. Once the coupling piece 13 is mounted over the spherical portion 11, the same is accommodated together with the bar that passes through the bore 22 and when the assembly is located on the desired position, the nut 14 is placed adjusting the coupling piece 13 against the screw 9 and the stud bolt 15 is adjusted to fasten the assembly to the corresponding bar 2–3.

Figure 7:
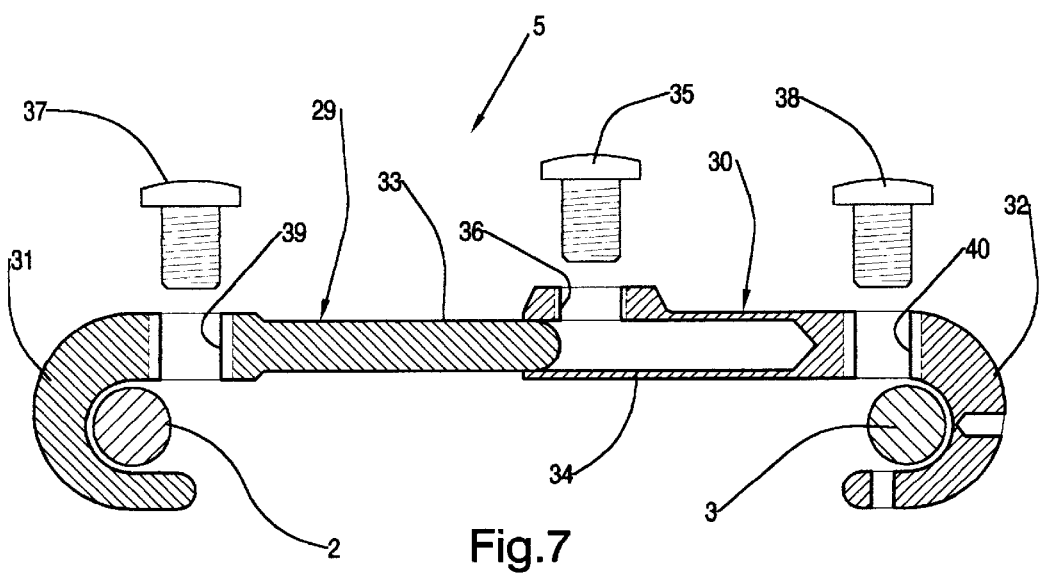
FIG. 7 shows a partial cross-sectional side-view, of a transverse linking bridge of the type comprising two telescopic parts, on which bridge such inserts of the invention are mounted.

Furthermore, the bars 2 and 3, are attached to each other by means of the transverse linking bridges 5 which are shown in general form in FIGS. 1, 2 y 3. In particular, a transverse linking bridge 5 according to the present invention is illustrated in FIGS. 7 to 10, which will be mentioned in the following. The transverse linking bridge 5 may be of the type consisting of an entire piece, elongated, with ends in form of a hook intended to attach to the bars 2 and 3, or may consist of two parts that attach telescopically to each other, as illustrated in FIG. 7, whereby the length limitation of a bridge with only one piece will not apply in this case and the distance between the bars 2 and 3 may be adjusted by means of the telescopical movement between both pieces. All the same, the advantages of the invention may be applied to any of these two types of bridge. Preferably, it will be referred in particular to a transverse linking bridge of telescopical type, of varying length. The telescopical transverse linking bridge 5, consists of two coupling parts 29 and 30 which allow the length of the bridge to be varied. Both parts present ends in form of hooks 31 and 32 destined to attach to the bars 2 and 3 as can be seen in FIG. 7, in cross section. The bridge part 29 presents a male elongated portion 33 entering in a female receptor portion 34 and may be firmly secured in position by the provision of a fixation screw 35 that adjusts inside a threaded bore 36 provided in the female receptor portion 34. In turn, the ends in form of a hook 31 and 32 remain firmly fastened to the bars 2 and 3 by a similar fastening mechanism by means of respective screws 37 and 38 that insert in the bores 39 and 40 so that the bars 2 and 32 are fixed and maintained in position.

Figure 8:
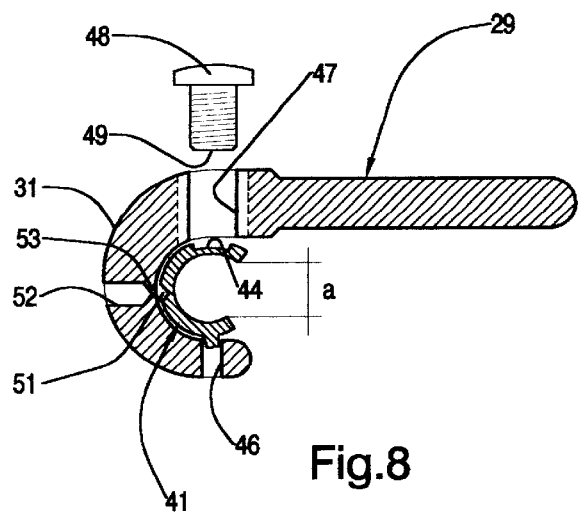
FIG. 8 shows a partial cross-sectional side view, that shows a spherical insert according to the invention, fitted on one of the linking bridge parts.
Figure 9:
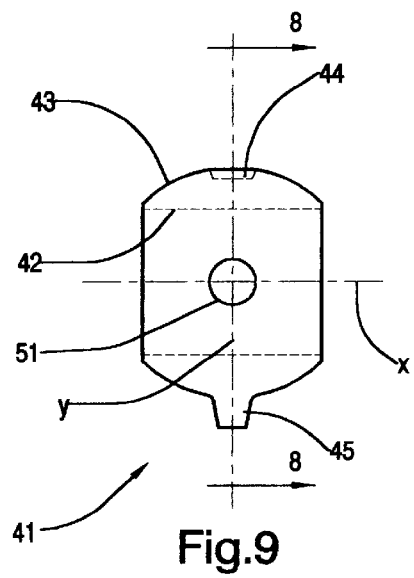
FIG. 9 shows a front view of the insert of FIG. 8, i.e., seen from its opened side or opening to receive the respective bar of the spine fixation arrangement.
Figure 10:
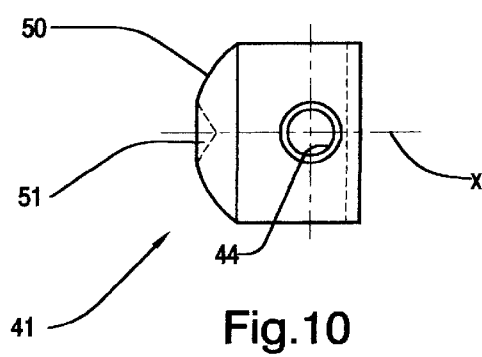
FIG. 10 shows a plan view of the insert of FIG. 9.

As illustrated in FIG. 8, the ends in form of hooks 31 and 32 include a spherical insert 41 illustrated independently in FIGS. 9 and 10, the object of which is to allow the accommodation of the movement of the bars 2 and 3 according to an angular movement in the plane that contains the same. Although in FIG. 8 a spherical insert 41 has been illustrated as placed in the bridge part 29, and more precisely at the hook end 31, the insert 41 may be mounted also at the end 32 to cooperate with the one mounted at the end 31.

The spherical insert 41 comprises a piece with a longitudinal passage of cylindrical section 42 and a spherical outer surface 43 intended to be fitted inside the hook 31 and 32 and to rotate inside the same around a longitudinal geometrical axis Y illustrated in FIG. 9. In the upper part the spherical insert 31 presents an assembly cavity 44 which will be mentioned in the following while the lower part of the insert 41 presents an assembly bolt protrusion 45, the function of which will be described with reference to FIG. 8.

The insert 41 is placed inside the hook 31 as illustrated in FIG. 8 for which the bolt 45 is inserted inside a bore 46 disposed in a lower leg of the hook end 31. An upper leg of the hook end 31 has a threaded bore 47 inside which a screw is inserted, preferably a stud bolt, which when threaded inside the bore 47 protrudes and its tip or lower end 49 is inserted inside the upper cavity 44 of the insert 41. Thus, the insert 41 remains fitted inside an inner surface of the hook 31 and may rotate around the geometrical axis Y due to the rotating assembly enabled by the bolt 45 and the bore 46, and the screw 48 inside the cavity 44. The spherical insert 41 presents a cross section in "C" form and the opening a (see FIG. 8) of the "C" is slightly smaller than the outer diameter of any of the bars 2 and 3. In this manner, once the insert 41 is pivotally mounted in the hook 31, the bar is inserted inside the insert 41 passing tightly through the opening a and remains fitted against the spherical inner surface 42 of the insert 41. That means, the "C" figure of the cross section of the insert 41 extends approximately along an angle of 224°.

Furthermore, the insert 41 has furthermore in a rear surface 50 an outer cavity 51 placed in an equatorial plane X of the insert 41. The cavity 51 cooperates with an outer cavity 52 also placed in the equatorial plane X of the hook 31 and matching with the cavity 51 of the insert 41. The cavity 52, in the hook 31, defines a thin wall thickness 53 able to be deformed by pressure or impact. The object of the cavities 51 and 52 is to define a lock between the hook end 31 and the spherical insert 41 to provide a predetermined limitation that will depend on the surface extension of the cavity 51. More precisely, once the bar 2 or 3 has been fixed to the spherical insert 41, this may be limited in its movement exerting a pressure against the thin wall 53, e.g., by means of a punch, or by impact of the punch inside the cavity 52, against the wall 53, so as to deform the wall 53 and create at the inner surface of the hook end 31 a protrusion that is introduced into the cavity 51 in the spherical insert 41 creating an interference between the wall of the hook end 31 and the spherical insert 41. Accordingly, the insert 41 will rotate in the proportion the opening size 51 allows the movement of the insert 41 which will be interrupted when the edges of the opening 51 interfere with the protrusion produced by the deformation in the wall 53 of the hook 31.

As can be seen, the bone fixation assembly according to the invention allows and easier and wider accommodation of all differences and deviations while placing the corresponding parts of the assembly, making the task of the professional easier when he must place the fixation arrangement in, for example, a spinal column.

I claim:

1. The combination of a bone fixation element and coupling piece for a spinal column fixation assembly, said bone fixation element comprising:
   (a) a screw or hook with a portion for fixing to the bone or part thereof;
   (b) an intermediate portion that is at least partially spherical, and
   (c) a threaded upper portion, said coupling piece comprising:
   (a) a seat portion having a concave inner surface for receiving said at least partially spherical intermediate portion of said bone fixation element, and a convex outer surface;
   (b) a throughbore through which said threaded upper portion of said bone fixation element extends;
   (c) a nut for coupling to said bone fixation element threaded upper portion to fasten said bone fixation element to said coupling piece, and
   (d) a bar fixation portion to be coupled to a bar.

2. The combination according to claim 1, wherein said nut has a concave surface coupling with said convex outer surface of said seat portion of said coupling piece.

3. The combination according to claim 2, wherein said nut has a gripping outer surface.

4. The combination according to claim 1, wherein said throughbore of said seat portion has a diameter larger than the diameter of said upper portion of said fixation element.

5. The combination according to claim 1, wherein said seat portion is linked through a bridge portion to said bar fixation portion.

6. The combination according to claim 5, wherein said bar fixation portion has a closed loop for passing the bar therethrough and a bore for the adjustment of a stud bolt for the retention of the bar.

7. The combination according to claim 5, wherein said bar fixation portion comprises an open groove for passing the bar therethrough and a bore for fixing a stud bolt for retaining the bar.

8. The combination according to claim 5, wherein said bar fixation portion and said seat portion are spaced apart end portions and are linked by said bridge portion.

9. The combination according to claim 1, wherein said throughbore of said seat portion and said inner surface of the seat portion and said at least partially spherical portion of said fixation element form a spherical coupling with an omnidirectional pivoting capacity of at least 12°.

10. The combination according to claim 1, wherein said fixation element is a screw.

11. The combination according to claim 1, wherein said fixation element is a hook.

12. A spinal column fixation assembly comprising:
   a bone fixation element having:
   (a) a screw or hook with a portion for fixing to the bone or part thereof;
   (b) an intermediate portion, and
   (c) an upper portion,
   a coupling piece having:
   (a) a seat portion having an inner surface for receiving said intermediate portion of said bone fixation element, and an outer surface;

(b) a throughbore through which said upper portion of said bone fixation element extends;

(c) a fastener for coupling to said bone fixation element upper portion to fasten said bone fixation element to said coupling piece, and (d) a bone fixation portion to be coupled to a bar;

a pair of bars;

a transverse linking bridge for fixation to said bars, including at least one coupling part to form a bridge of adjustable length, the bridge including ends having a hook-shape for coupling to the respective bars of the fixation assembly, wherein at least one of said hook ends has an insert having an at least partially spherical outer surface pivotally mounted in said one hook, said insert including a fitting inner surface for each one of said bars.

13. A transverse linking bridge for fixation to bars of a spine fixation assembly including at least one coupling part to form a bridge of adjustable length, the bridge including ends having a hook-shape for coupling to the respective bars of the fixation assembly, wherein at least one of said hook ends has an insert having an at least partially spherical outer surface pivotally mounted in said at least one hook end, said insert including a fitting inner surface for each one of the bars of the spine fixation assembly.

14. A transverse linking bridge according to claim 13, wherein each one of said hook ends has a C-shaped longitudinal section and the upper and the lower legs of the "C" have respective upper and lower assembly bores for said spherical insert.

15. A transverse linking bridge according to claim 14, wherein said lower assembly bore is a recess receiving a rotating bolt that projects from a lower part of said spherical insert, said recess and said bolt defining a lower rotating assembly of said insert inside said C-shaped hook.

16. A transverse linking bridge according to claim 15, wherein said upper assembly bore is a throughbore which receives a rotating screw having an end that, after being threaded inside the bore, passes through the bore and remains located inside a cavity placed at the upper outer surface of said spherical insert, forming said upper cavity and said pivoting screw end, placed in the cavity, an upper pivoting assembly of said insert inside said C-shaped hook.

17. A transverse linking bridge according to claim 16, wherein said upper and lower pivoting assemblies are arranged in a diametric opposite configuration in the outer surface of the insert.

18. A transverse linking bridge according to claim 14, wherein the cross-sectional C-shape of the hook end extends along at least 224° to define an interference fit with the associated bar.

19. A transverse linking bridge according to claim 14, wherein the insert includes an outer cavity located at an equatorial plane of the insert, and the C-shaped hook end has an outer cavity coincident with the cavity of the insert, the outer cavity of the hook end having a thin wall capable of being deformed by pressure to enter into the cavity of the insert.

20. A transverse linking bridge according to claim 13, wherein the bridge comprises two telescopic parts.

* * * * *